(12) United States Patent
Wang et al.

(10) Patent No.: US 9,856,183 B2
(45) Date of Patent: Jan. 2, 2018

(54) CATALYST WITH HIGH C4 OLEFIN SELECTIVITY FOR PREPARING OLEFIN FROM METHANOL AND PREPARATION METHOD THEREOF

(71) Applicant: SHANGHAI BI KE CLEAN ENERGY TECHNOLOGY CO., LTD, Shanghai (CN)

(72) Inventors: Yijun Wang, Shanghai (CN); Guo Rui, Shanghai (CN); Fan Zhang, Shanghai (CN); Yongsheng Gan, Shanghai (CN); Xiaomang Zhang, Shanghai (CN)

(73) Assignee: SHANGHAI BI KE CLEAN ENERGY TECHNOLOGY CO., LTD., Shanghai (CN)

( * ) Notice: Subject to any disclaimer, the term of this patent is extended or adjusted under 35 U.S.C. 154(b) by 10 days.

(21) Appl. No.: 14/764,923

(22) PCT Filed: Jan. 29, 2014

(86) PCT No.: PCT/CN2014/071747
§ 371 (c)(1),
(2) Date: Jul. 30, 2015

(87) PCT Pub. No.: WO2014/117740
PCT Pub. Date: Aug. 7, 2014

(65) Prior Publication Data
US 2015/0367333 A1     Dec. 24, 2015

(30) Foreign Application Priority Data
Jan. 31, 2013 (CN) .......................... 2013 1 0040941

(51) Int. Cl.
| C07C 1/20 | (2006.01) |
|---|---|
| B01J 29/40 | (2006.01) |
| B01J 37/00 | (2006.01) |
| B01J 21/12 | (2006.01) |
| B01J 21/16 | (2006.01) |
| B01J 27/16 | (2006.01) |
| B01J 35/00 | (2006.01) |
| B01J 35/02 | (2006.01) |
| B01J 37/04 | (2006.01) |
| B01J 37/28 | (2006.01) |
| B01J 37/08 | (2006.01) |

(52) U.S. Cl.
CPC ................. C07C 1/20 (2013.01); B01J 21/12 (2013.01); B01J 21/16 (2013.01); B01J 27/16 (2013.01); B01J 29/40 (2013.01); B01J 35/0006 (2013.01); B01J 35/026 (2013.01); B01J 37/0045 (2013.01); B01J 37/0072 (2013.01); B01J 37/04 (2013.01); B01J 37/0018 (2013.01); B01J 37/082 (2013.01); B01J 37/28 (2013.01); B01J 2229/20 (2013.01); B01J 2229/42 (2013.01); C07C 2529/40 (2013.01); Y02P 20/52 (2015.11)

(58) Field of Classification Search
CPC ...................................................... C07C 1/20
See application file for complete search history.

(56) References Cited

U.S. PATENT DOCUMENTS 6,538,167 B1    3/2003   Brown et al.

FOREIGN PATENT DOCUMENTS

| CN | 101172918 A | 5/2008 | |
|---|---|---|---|
| CN | 101274283 A | 10/2008 | |
| CN | 101279280 A | 10/2008 | |
| CN | 101318143 A | 12/2008 | |
| CN | 101402049 A | 4/2009 | |
| CN | 102211971 A | 10/2011 | |
| CN | 102371168 A | 3/2012 | |
| CN | 102372534 A | 3/2012 | |
| CN | 102531823 A | 7/2012 | |
| CN | 103623859 A | 3/2014 | |
| DE | 2935863 A1 * | 3/1980 | .............. B01J 29/40 |
| WO | 0232836 A1 | 4/2002 | |
| WO | 2004018089 A1 | 3/2004 | |

OTHER PUBLICATIONS

Machine translation CN 101318143. Dec. 10, 2008.*
Machine translation DE 2935863. Mar. 13, 1980 (Year: 1980).*
First Search Report and Office Action received in connection with CN Application No. 201310040941.3 dated Sep. 1, 2015, 7 pages.
Second Search Report and Office Action received in connection with CN Application No. 201310040941.3 dated Apr. 15, 2016, 9 pages.
International Search Report and Written Opinion and translation for PCT/CN2014/071747, dated Apr. 30, 2014, 5 pages.

* cited by examiner

Primary Examiner — Sharon Pregler
Assistant Examiner — Alyssa L Cepluch
(74) Attorney, Agent, or Firm — Hovey Williams LLP

(57) ABSTRACT

A method of preparing a catalyst, comprising: (1) mixing a ZSM-5 molecular sieve, a phosphorus source, a matrix material, a bonding agent and water to formulate an aqueous slurry, wherein the total content of the components except for water is 20-50 wt % based on the total weight of the aqueous slurry; (2) spray drying the slurry obtained in step (1) to obtain a granular intermediate product; and (3) calcining the granular intermediate product obtained in step (2) to obtain the catalyst used for preparing olefin from methanol in a fluid bed. The invention also provides a catalyst prepared according to said method, and a process of preparing olefin from methanol using said catalyst. In the methanol-to-olefin process, the conversion of methanol is >99%; the propylene selectivity is high; and the C4 selectivity is up to 32%.

3 Claims, No Drawings

CATALYST WITH HIGH C4 OLEFIN SELECTIVITY FOR PREPARING OLEFIN FROM METHANOL AND PREPARATION METHOD THEREOF

RELATED APPLICATION

The present application is a national stage application under 35 U.S.C §371 of International Application No. PCT/CN2014/071747, filed Jan. 29, 2014, which is incorporated by reference herein in its entirety.

TECHNICAL FIELD

The invention generally relates to the catalytic field, more particularly to a method of preparing a catalyst used to prepare olefin from methanol in a fluid bed reactor, wherein the catalyst prepared by this method has very high C4 olefin selectivity.

BACKGROUND ART

Ethylene, propylene and butadiene are important chemical raw materials, and are generally obtained by pyrolysis or steam cracking of naphtha. At present, the main source of propylene includes propylene co-produced with ethylene and propylene as a refinery byproduct. The main source of butadiene is by further processing the C4 byproducts produced in an ethylene cracking process. However, these manners of production can hardly meet the increasing demand for propylene and butadiene in China. It has been highly desirable to develop a process for preparing propylene and C4 olefin at high selectivity.

As such, the researchers in Dalian Institute of Chemical Physics have developed a DMTO technology which uses an aqueous solution of methanol as raw material in a reaction in the presence of a catalyst of SAPO-34 molecular sieve. The main products are ethylene and propylene, but the selectivity to C4 olefin is very low, more particularly, only less than 10%.

According to the fixed-bed technology for preparing olefin from methanol developed by Lurgi Co., Germany (WO2004/018089), a ZSM-5 molecular sieve purchased from Süd-Chemie Co. is used as a catalyst to carry out the reaction for preparing olefin from methanol in a fixed-bed reactor, and the resultant selectivity to propylene is 35-40%. CN102531823A, CN101172918B, CN101279280B, CN101402049A, CN102211971A disclose respectively processes for preparing propylene from methanol in fixed-bed reaction systems and methods for preparing catalysts. More particularly, these processes mainly improve the single-pass selectivity to propylene by modifying a ZSM-5 molecular sieve which acts as an active component. However, most of these patent applications focus on improving the single-pass selectivity to propylene, but neglect the selectivity to C4 olefin. In the Lurgi process which has already been put into real industrial use, C4 and C5 olefins are recycled to the MTP reactor for continuing reaction to produce propylene.

In a research report, there is reported a technique for preparing a catalyst used to prepare olefin from methanol in a fluid bed, wherein a ZSM-5 molecular sieve is used as the active component, and modifiers such as rare earth modifier, alkaline modifier and like are added to improve the activity of the molecular sieve. An aqueous solution of methanol is used as a raw material, and the catalyst is used to carry out a reaction where the resultant propylene selectivity is up to 55%, whereas the C4 selectivity is not high, only 25%.

As can be seen, the previous research on the process of preparing olefin from methanol mainly concentrates on improving the single-pass selectivity to propylene and the propylene/ethylene ratio in the products, whereas the selectivity to C4 products is not a focus. The practice of recycling the C4 products to the reactor for continuing reaction and producing propylene in the MTP process complicates the process, and it's very difficult to guarantee the selectivity to propylene. On the other hand, there is a high demand for butadiene in the domestic market, and thus the market price of butadiene has been high for a long time. If a methanol-to-olefin reaction can be enabled to have high C4 olefin selectivity while the high selectivity to the propylene product is ensured, and butadiene is produced by separating butene from the C4 olefin products and dehydrogenating the butene, additional and high economic profit will be obtained.

SUMMARY

In view of the above technical problems, the present invention develops a novel catalyst prepared by a forming method in which a ZSM-5 molecular sieve is used as an active component and mixed with a matrix material, a bonding agent, a pore former and a phosphorus source, followed by spray drying to produce the catalyst. As compared with a traditional catalyst for preparing olefin from methanol, the catalyst of the invention has a C4 selectivity up to 32%, while still having a rather high propylene selectivity. Additionally, the catalyst of the invention has high mechanical strength and abrasion resistance, and is very suitable for use in a fluid bed system.

According to a first aspect of the invention, there is provided a method of preparing a catalyst used for preparing olefin from methanol in a fluid bed, comprising:

(1) mixing a ZSM-5 molecular sieve, a phosphorus source, a matrix material, a bonding agent and water to formulate an aqueous slurry, wherein the total content of the components except for water is 20-50 wt % based on the total weight of the aqueous slurry;

(2) spray drying the slurry obtained in step (1) to obtain a granular intermediate product; and (3) calcining the granular intermediate product obtained in step (2) to obtain the catalyst used for preparing olefin from methanol in a fluid bed.

In an embodiment of the invention, the silica to alumina ratio of the ZSM-5 molecular sieve is 20-400, preferably 200-400; and the content of the ZSM-5 molecular sieve is 20-55 wt % based on the total weight of the components except for water in the aqueous slurry.

In an embodiment of the invention, the matrix material is selected from one or more of kaolin clay, calcined kaolin clay, diatomaceous earth, pseudo boehmite and montmorillonite; and the matrix material has a particle diameter of less than 2 μm, and a content of 20-59 wt % based on the total weight of the components except for water in the aqueous slurry.

In an embodiment of the invention, the bonding agent is selected from one or more of alkaline silica sol, acidic silica sol, alumina sol, aluminum phosphate, aluminum nitrate and aluminum oxide; and the bonding agent has a content of 20-50 wt % based on the total weight of the components except for water in the aqueous slurry.

In an embodiment of the invention, the phosphorus source is selected from one or more of phosphoric acid, phosphorous acid, ammonium hydrogen phosphate, ammonium dihydrogen phosphate and ammonium phosphate; and the phosphorus source has a content of 0.1-5.0 wt % based on the total weight of the components except for water in the aqueous slurry.

In an embodiment of the invention, the slurry further comprises a pore former, wherein the pore former is selected from one or more of sesbania powder, polyvinyl alcohol and methyl cellulose; and the pore former has a content of 0.01-1 wt % based on the total weight of the components in the aqueous slurry except for water.

In an embodiment of the invention, in step (2), a centrifugal spray dryer or a pressure spray dryer is used for spray drying, wherein the spray dryer has an inlet temperature of 150-300° C. and an outlet temperature of 120-250° C., and the slurry is fed into the spray dryer at a rate of 100-500 ml/min.

In an embodiment of the invention, in step (3), the granular intermediate product is calcined at 550-650° C., preferably at 600° C. for 3-6 hours, preferably 4 hours.

The second aspect of the invention relates to a catalyst for preparing olefin from methanol in a fluid bed, wherein the catalyst is prepared according to the method of the invention, and the catalyst comprises 25-60 wt %, preferably 25-40 wt % of A ZSM-5 molecular sieve, 0.05-3 wt % of a component derived from the phosphorus source, 20-50 wt %, preferably 30-45 wt % of a component derived from the matrix material, and 10-45 wt %, preferably 25-40 wt % of a component derived from the bonding agent, wherein the catalyst has a particle diameter of 50-110 μm.

The third aspect of the invention relates to a process of preparing olefin from methanol, comprising: contacting methanol or an aqueous solution of methanol with the catalyst prepared according to the method of the invention in a fluid bed reactor under reaction conditions that are sufficient to convert methanol to olefin, wherein the reaction conditions are as follows: mass space velocity of methanol 0.5-5 $h^{-1}$, reaction temperature 430-550° C., reaction pressure 0-1.0 MPa; wherein the selectivity to propylene in the products is more than 40%, preferably more than 45%; and the selectivity to olefins having four carbons is more than 25%, preferably more than 28%, more preferably more than 30%, most preferably up to 32%.

The catalyst shows remarkably increased selectivity to C4 products owing to the modification by phosphorus. Additionally, the catalyst of the present application can be suitably used as a fluid bed catalyst and has no reduction in its abrasion resistance.

DETAILED DESCRIPTION OF THE INVENTION

A "range" disclosed herein is defined by a lower limit and/or an upper limit. It may comprise one or more lower limits and/or one or more upper limits. A given range is defined by selecting one lower limit and one upper limit. The selected lower limit and upper limit define the boundary of a particular range. All ranges that may be defined this way are inclusive and combinable, i.e. any lower limit may be combined with any upper limit to form a new range. For example, when ranges of 60-120 and 80-110 are given for a particular parameter, it shall be understood that ranges of 60-110 and 80-120 are also contemplated. In addition, if 1 and 2 are listed as the minimum value, and 3, 4 and 5 are listed as the maximum value, then the following ranges are all contemplated: 1-3, 1-4, 1-5, 2-3, 2-4 and 2-5.

In the invention, a numerical range of "a-b" is a simplified representation of the combination of any real number between a and b, wherein both a and b are real numbers, unless otherwise specified. For example, the numerical range of "0-5" is intended to mean that all real numbers between "0-5" are disclosed herein, wherein "0-5" is only a simplified representation of the combinations of these numeral.

If not specified particularly, the term "two" as used herein refers to "at least two".

In the invention, if not specified particularly, all the embodiments and preferred embodiments mentioned herein may be combined with each other to form new technical solutions.

In the invention, if not specified particularly, all the technical features and preferred features mentioned herein may be combined with each other to form new technical solutions.

In the invention, if not specified particularly, all the steps mentioned herein may be conducted in sequence or randomly, but preferably in sequence. For example, when a method comprises steps (a) and (b), it means that this method comprises steps (a) and (b) conducted sequentially, or steps (b) and (a) conducted sequentially. For example, if the method mentioned above further comprises step (c), it means that step (c) may be incorporated into the method in any sequence. For example, the method may comprise steps (a), (b) and (c), or steps (a), (c) and (b), or steps (c), (a) and (b), etc.

In the invention, if not specified particularly, the term "comprise" mentioned herein defines both the open and closed ended modes. For example, the term "comprise" means that other elements which are not listed can also be included, or that only those elements which are listed are exclusively included.

The catalyst of the invention can be used in the methanol-to-olefin reaction and provide very high C4 selectivity. In the invention, C4 component or C4 product refers to all the components having four carbons in the reaction product, mostly C4 olefin. Thus, the terms "C4 component", "C4 product" and "C4 olefin" may be used exchangeably to represent the same components in the product. The C4 olefin used herein may include 1-butene, 2-butene, 1,3-butadiene, 2-methyl-1-propylene, etc. Isomers such as 1-butene, 2-butene, 2-methyl-1-propylene and like may be used to prepare 1,3-butadiene by subsequent operations such as dehydrogenation or isomerization, etc. As such, the catalyst of the invention may be used to obtain two products of high economic value at high selectivity in a single reaction.

The active component in the catalyst of the invention is a ZSM-5 molecular sieve which, as a molecular sieve catalytic material well known in the art, may be purchased directly in the market, or synthesized according to literature methods. The ZSM-5 molecular sieve used in the following Examples of the invention has a silica to alumina ratio of 20-400, preferably 200-400.

By doping the catalyst of the invention with a small amount of phosphorus, the desired high C4 olefin selectivity may be obtained while the high propylene selectivity is maintained. Phosphorus is introduced into the catalyst from a phosphorus source, wherein the phosphorus source is selected from one or more of phosphoric acid, phosphorous acid, ammonium hydrogen phosphate, ammonium dihydrogen phosphate and ammonium phosphate. In the subsequent spray drying and calcining processes, these phosphorus sources may form $P_2O_5$ supported on the ZSM-5 molecular sieve; alternatively, P may also be incorporated into the skeleton of the molecular sieve by substituting Si or Al with P.

The matrix material used to prepare the catalyst of the invention is one or more of kaolin clay, calcined kaolin clay, diatomaceous earth, pseudo boehmite and montmorillonite, and has a particle diameter of less than 2 µm. The matrix material functions to improve the strength and abrasion resistance of the catalyst. In the course of calcining, the matrix material may be dehydrated and/or decomposed to certain extent. For example, pseudo boehmite may be dehydrated during calcining and form alumina It is also possible that a portion of the matrix material is not dehydrated and/or decomposed. In the invention, all these components in the product catalyst are collectively termed as "the component derived from the matrix material".

The catalyst of the invention comprises 10-45 wt % of a component derived from the bonding agent, wherein the component is residual substance of the bonding agent after spray drying and calcining. The bonding agent can improve the homogeneity and fluid behavior of the whole slurry system at the stage of slurry, and facilitate improvement in the whole mechanical strength of the catalyst obtained finally and significant improvement in its abrasion resistance. The composition of the bonding agent may be controlled by adjusting the category and amount of the bonding agent as desired particularly. The precursor used in the invention is selected from one or more of the following materials: alkaline silica sol, acidic silica sol, alumina sol, aluminum phosphate, aluminum nitrate, aluminum oxide, etc. The alumina may be amorphous alumina. The alkaline silica sol refers to a sol formed by silicon dioxide particles in water, wherein the silicon dioxide has an average particle diameter of 8-20 µm. The pH of the alkaline silica sol is 9-10, wherein the molecular formula of the silicon dioxide is $SiO_2 \cdot nH_2O$. Based on the total weight of the silica sol, the silica sol, when calculated in the form of oxides, comprises 15-40 wt % silicon dioxide, 0.2-0.4 wt % $Na_2O$, and the balance of water. The alkaline silica sol has a viscosity (25° C.) of 2-2.5 MPa·s and a density (25° C.) of 1.1-1.3 g/cm$^3$. Acidic silica sol is also called hydrosol of silicic acid. It is an acidic colloid formed from high molecular silicon dioxide particles dispersed in water. Its pH value is 2-4. Based on the total weight of the acidic silica sol, the silica sol, when calculated in the form of oxides, comprises 30-31 wt % silicon dioxide, less than 0.006 wt % $Na_2O$, and the balance of water. The acidic silica sol has a viscosity (25° C.) of less than 6 MPa·s and a density (25° C.) of 1.19-1.21 g/cm$^3$. The average particle diameter of the silicon dioxide particles is 5-20 nm. The acidic silica sol may stand stably under ambient conditions for three months without formation of any precipitate. Alumina sol is a colloid formed from aluminum oxide particles in water, wherein the solid content is 10-40 wt %, pH is 1-3, the average particle diameter of the aluminum oxide particles is 10-50 nm, and the chemical formula of the aluminum oxide particles may be written as $Al_2O_3 \cdot nH_2O$.

The method used for preparing the catalyst of the invention comprises mixing a ZSM-5 molecular sieve, a phosphorus source, a matrix material, a bonding agent, an optional pore former and water to formulate an aqueous slurry, followed by spray drying and calcining the slurry. Based on the total weight of the aqueous slurry, the total content of the components except for water is 20-50 wt %. The pore former is a material that can be burned off completely during calcining and thus leaving pores of desired size in the catalyst. The pore former is mainly used to form pores in the catalyst, and thus increasing the contact area between the catalyst and the reactant materials. Pore forming materials known in the art may be used, such as starch, graphite, etc., but sesbania powder, polyvinyl alcohol and methyl cellulose are preferred for use. The pore former is used at a small amount to avoid influence on the catalytic performance of the catalyst and prevent incomplete burning of the pore former during calcining. Based on the total weight of the components except for water in the aqueous slurry, the pore former has a content of 0.01-1 wt %.

The above aqueous slurry is spray dried using a spray dryer according to the invention. In the course of spray drying, the slurry is atomized in a drying chamber, and then the slurry drops contacted with hot air to vaporize the water therein rapidly, so as to obtain a dry product having substantially homogeneous particle size and shape. A centrifugal spray dryer or a pressure spray dryer is preferably used for spray drying according to the invention. These two types of spray dryers differ from each other in the manner for atomizing the slurry. In the centrifugal spray dryer, the slurry is delivered to a centrifugal turntable rotating at high speed in an atomizer, so that the slurry is thrown off at high speed and thus atomized The pressure spray dryer uses a high pressure pump to jet the slurry into a drying chamber to atomize it.

EXAMPLES

The invention will be further illustrated with reference to the following examples. In the following examples, the ZSM-5 catalyst used has a silica/alumina ratio of 20-400, preferably 250-400. The alkaline silica sol is a silica sol having a solid concentration of 30 wt % and pH of 9, wherein the average particle diameter of the solid particles is 14 nm. The acidic silica sol is a silica sol having a solid concentration of 30 wt % and pH of 2, wherein the average particle diameter of the solid particles is 14 nm. The alumina sol is an alumina sol having a solid concentration of 30 wt % and pH of 2, wherein the average particle diameter of the solid particles is 20 nm. The polyvinyl alcohol is obtained commercially and has a molecular weight of 16000-20000. Kaolin clay, pseudo boehmite, sesbania powder, $H_3PO_4$, calcined kaolin clay, diatomaceous earth, ammonium phosphate, ammonium hydrogen phosphate, ammonium dihydrogen phosphate, montmorillonite and methanol are all obtained commercially and used directly without further purification.

Example 1

Into a 5 L stainless steel reactor was added 4000 g water, then 600 g ZSM-5 catalyst powder (silica/alumina ratio: 250) under full agitation for 30 min, then sequentially 1200 g alkaline silica sol, 600 g kaolin clay, 400 g pseudo boehmite, 2 g sesbania powder and 4000 g deionized water, followed by full agitation to prepare an aqueous slurry. A centrifugal spray dryer was used to spray dry the aqueous slurry, wherein the centrifugal spray dryer had an inlet temperature of 300° C. and an outlet temperature of 180° C., and the feeding speed of the aqueous slurry was 100 ml/min. The particles obtained after the spray drying were calcined in a muffle furnace at 650° C. in air atmosphere for 2 h to obtain Catalyst 1#.

Example 2

Into a 5 L stainless steel reactor was added 4000 g water, then 600 g ZSM-5 catalyst powder (silica/alumina ratio: 300) under full agitation for 30 min, then sequentially 1200 g alkaline silica sol, 600 g kaolin clay, 400 g pseudo boehmite, 2 g sesbania powder, 50 g H₃PO₄ and 4000 g deionized water, followed by full agitation to prepare an aqueous slurry. A centrifugal spray dryer was used to spray dry the aqueous slurry, wherein the centrifugal spray dryer had an inlet temperature of 300° C. and an outlet temperature of 180° C., and the feeding speed of the aqueous slurry was 100 ml/min. The particles obtained after the spray drying were calcined in a muffle furnace at 650° C. in air atmosphere for 2 h to obtain Catalyst 2#.

Example 3

Into a 5 L stainless steel reactor was added 4000 g water, then 1000 g ZSM-5 catalyst powder (silica/alumina ratio: 350) under full agitation, then 750 g acidic silica sol, 1200 g calcined kaolin clay, 900 g pseudo boehmite, 10 g sesbania powder and 5 g ammonium dihydrogen phosphate, followed by full agitation to prepare an aqueous slurry. A centrifugal spray dryer was used to spray dry the aqueous slurry, wherein the centrifugal spray dryer had an inlet temperature of 300° C. and an outlet temperature of 180° C., and the feeding speed of the aqueous slurry was 250 ml/min. The particles obtained after the spray drying were calcined in a muffle furnace at 600° C. in air atmosphere for 4 h to obtain Catalyst 3#.

Example 4

Into a 5 L stainless steel reactor was added 5000 g water, then 700 g ZSM-5 catalyst powder (silica/alumina ratio: 400) under full agitation, then 900 g alumina sol, 100 g acidic silica sol, 1400 g diatomaceous earth, 30 g sesbania powder and 180 g ammonium hydrogen phosphate, followed by full agitation to prepare an aqueous slurry. A centrifugal spray dryer was used to spray dry the aqueous slurry, wherein the centrifugal spray dryer had an inlet temperature of 300° C. and an outlet temperature of 180° C., and the feeding speed of the aqueous slurry was 250 ml/min. The particles obtained after the spray drying were calcined in a muffle furnace at 600° C. in air atmosphere for 4 h to obtain Catalyst 4#.

Example 5

Into a 5 L stainless steel reactor was added 5000 g water, then 3000 g ZSM-5 catalyst powder (silica/alumina ratio: 300) under full agitation, then 600 g alkaline silica sol, 1400 g kaolin clay, 600 g pseudo boehmite, 10 g polyvinyl alcohol and 10 g ammonium phosphate, followed by full agitation to prepare an aqueous slurry. A centrifugal spray dryer was used to spray dry the aqueous slurry, wherein the centrifugal spray dryer had an inlet temperature of 300° C. and an outlet temperature of 180° C., and the feeding speed of the aqueous slurry was 250 ml/min. The particles obtained after the spray drying were calcined in a muffle furnace at 600° C. in air atmosphere for 4 h to obtain Catalyst 5#.

Example 6

Into a 5 L stainless steel reactor was added 12000 g water, then 900 g ZSM-5 catalyst powder (silica/alumina ratio: 250) under full agitation, then 1600 g acidic silica sol, 800 g montmorillonite, 5 g sesbania powder and 40 g phosphoric acid, followed by full agitation to prepare an aqueous slurry. A centrifugal spray dryer was used to spray dry the aqueous slurry, wherein the centrifugal spray dryer had an inlet temperature of 300° C. and an outlet temperature of 180° C., and the feeding speed of the aqueous slurry was 250 ml/min. The particles obtained after the spray drying were calcined in a muffle furnace at 600° C. in air atmosphere for 4 h to obtain Catalyst 6#.

The catalyst prepared in Example 1 was not doped with phosphorus, and is used as a control. Examples 2-6 represent catalysts of the invention. In the following Example 7, the catalytic performances of these catalysts were characterized.

Example 7

150 g of one of the above catalysts 1#-6# was weighed and charged into a fluid bed having a diameter of 50 mm and a height of 110 cm. An aqueous solution of methanol having a concentration of 50% by volume was used as a feedstock. The temperature of the reactor was 460-500° C., the mass space velocity of the methanol was 2h⁻¹, and the reaction pressure was 0.1 MPa. The compositions of the products obtained in the reaction using these catalysts were determined by gas chromatography. The conversion of methanol was determined to be 100%. Eight hours after the reaction began, the specific product distributions were shown in Table 1.

TABLE 1

Product distribution (by mass percentages) versus catalyst in methanol-to-olefin reaction

| No. | CH4 | C2H4 | C3H6 | C4 | C5 |
|---|---|---|---|---|---|
| 1# | 1.65 | 9.44 | 45.27 | 25.74 | 13.04 |
| 2# | 1.76 | 10.34 | 45.88 | 32.14 | 8.56 |
| 3# | 2.30 | 12.30 | 46.60 | 29.90 | 6.99 |
| 4# | 2.13 | 11.59 | 45.91 | 30.34 | 7.34 |
| 5# | 2.03 | 10.97 | 46.56 | 28.42 | 8.27 |
| 6# | 2.16 | 13.44 | 44.51 | 28.47 | 10.21 |

As indicated by the above table, in comparison with Catalyst 1# without phosphorus doping, the catalysts of the invention exhibit significant improvement in terms of selectivity to propylene and C4 olefin.

Example 8

A vertical abrasion index tester was used to test the abrasion indices of Catalysts 1# and 2#, wherein ASTM-D5757-00 was used as the standard, and a FCC equilibrium catalyst available from Changling Petrochemical Co. was used as a control. The abrasion index was 2.5% for the Changling FCC equilibrium catalyst, 2.1% for Catalyst 1#, and 1.9% for Catalyst 2#. As can be seen, the catalyst of the invention also shows remarkably increased abrasion resistance due to doping of phosphorus.

What is claimed is:

1. A process of preparing olefin products from methanol, comprising: contacting methanol or an aqueous solution of methanol with a catalyst in a fluid bed reactor under reaction conditions that are sufficient to convert methanol to olefin products, wherein the reaction conditions include: mass space velocity of methanol 0.5-5 h⁻¹, reaction temperature 430-550° C., reaction pressure 0-1.0 MPa; wherein the selectivity to propylene in the olefin products is more than 40%; and the selectivity to olefins having four carbons is more than 25%, wherein the catalyst comprises 25-60 wt % of a ZSM-5 molecular sieve, 0.05-3 wt % of a component derived from a phosphorus source, 20-50 wt % of a component derived from a matrix material, and 10-45 wt % of a component derived from a bonding agent, wherein the catalyst has a particle diameter of 50-110 μm, and the catalyst is prepared by a method comprising the steps of:

(1) mixing the ZSM-5 molecular sieve, the phosphorus source, the matrix material, the bonding agent and water to formulate an aqueous slurry, wherein the total content of the components except for water is 20-50 wt % based on the total weight of the aqueous slurry;

(2) spray drying the slurry obtained in step (1) to obtain a granular intermediate product; and (3) calcining the granular intermediate product obtained in step (2) to obtain the catalyst that can be used for preparing olefin from methanol in a fluid bed, wherein the ZSM-5 molecular sieve has a silica to alumina ratio of 200-400.

2. The process of claim 1, wherein the selectivity to propylene in the olefin products is more than 45%; and the selectivity to olefins having four carbons is more than 28%.

3. The process of claim 1, wherein the selectivity to propylene in the olefin products is more than 45%; and the selectivity to olefins having four carbons is more than 30%.

* * * * *